US008921081B2

(12) United States Patent
Suzuki et al.

(10) Patent No.: US 8,921,081 B2
(45) Date of Patent: Dec. 30, 2014

(54) POWDERY LIPASE PREPARATION, METHOD FOR PRODUCING THE SAME AND USE THEREOF

(75) Inventors: Junko Suzuki, Yokosuka (JP); Yoshie Yamauchi, Yokosuka (JP); Tamami Manabe, Yokosuka (JP); Satoshi Negishi, Yokosuka (JP)

(73) Assignee: The Nisshin Oillio Group, Ltd., Chuo-Ku, Tokyo (JP)

( * ) Notice: Subject to any disclaimer, the term of this patent is extended or adjusted under 35 U.S.C. 154(b) by 543 days.

(21) Appl. No.: 12/531,327

(22) PCT Filed: Mar. 12, 2008

(86) PCT No.: PCT/JP2008/054448
§ 371 (c)(1),
(2), (4) Date: Sep. 15, 2009

(87) PCT Pub. No.: WO2008/114656
PCT Pub. Date: Sep. 25, 2008

(65) Prior Publication Data
US 2010/0112650 A1 May 6, 2010

(30) Foreign Application Priority Data
Mar. 16, 2007 (JP) .................................. 2007-069189

(51) Int. Cl.
*C12P 7/64* (2006.01)
*C12N 9/20* (2006.01)
*C12P 7/62* (2006.01)

(52) U.S. Cl.
CPC .... *C12N 9/20* (2013.01); *C12P 7/62* (2013.01)
USPC ........................................................ 435/134

(58) Field of Classification Search
None
See application file for complete search history.

(56) References Cited

U.S. PATENT DOCUMENTS

| 3,660,571 | A | * | 5/1972 | Kodama ........................... 514/29 |
| 4,798,793 | A | | 1/1989 | Eigtved |
| 5,166,064 | A | | 11/1992 | Usui et al. |
| 5,480,787 | A | | 1/1996 | Negishi et al. |
| 6,162,623 | A | | 12/2000 | Grote et al. |
| 6,399,059 | B1 | | 6/2002 | Minoshima et al. |
| 2006/0105438 | A1 | | 5/2006 | Suzuki et al. |
| 2006/0105935 | A1 | | 5/2006 | Suzuki et al. |
| 2007/0155003 | A1 | | 7/2007 | Suganuma et al. |
| 2008/0280020 | A1 | * | 11/2008 | Kugitani et al. ............... 426/634 |
| 2009/0104680 | A1 | | 4/2009 | Suzuki et al. |
| 2009/0136619 | A1 | | 5/2009 | Uehara et al. |

FOREIGN PATENT DOCUMENTS

| CN | 1806043 A | 7/2006 |
| EP | 0 140 542 A | 5/1985 |
| EP | 2 042 607 | 4/2009 |
| JP | 60-098984 A | 6/1985 |
| JP | 61-202688 A | 9/1986 |
| JP | 62-138191 | 6/1987 |
| JP | 62-269685 A | 11/1987 |
| JP | 01-262795 A | 10/1989 |
| JP | 02-138986 A | 5/1990 |
| JP | 03-061485 A | 3/1991 |
| JP | 11-246893 A | 9/1999 |
| JP | 2000-106873 A | 4/2000 |
| JP | 2001-178488 | 7/2001 |
| JP | 3403202 B | 2/2003 |
| JP | 2006-325465 A | 12/2006 |
| JP | 2007-068426 A | 3/2007 |
| RU | 2 233 325 C1 | 7/2004 |
| WO | WO 97/01632 A1 | 1/1997 |
| WO | WO 2006/030889 A1 | 3/2006 |
| WO | WO2006098399 | 9/2006 |
| WO | WO 2008/010543 A1 | 1/2008 |

OTHER PUBLICATIONS

English-language translation of the Abstract for Japanese Patent Publication No. 61-202688.
Supplementary European Search Report issued in the corresponding Application No. 08721864.0-2405 dated Apr. 29, 2010.
Xuehao Yang et al., *Production of lipase by repeated batch fermentation with immobilized Rhizopus arrhizus*, 40(6) Process Biochemistry 2095-2103 (2005).
* International Search Report (PCT/ISA/210) for PCT/JP2008/054448 mailed May 27, 2008.
* Written Opinion (PCT/ISA/237) for PCT/JP2008/054448 mailed May 27, 2008.
English translation of Russian Decision of Patent Grant dated Oct., 11, 2011, for corresponding Russian Application Serial No. 2009138225/10(054103).
Grachyova et al., *Technology of enzymatic preparations*, P "Elevar", 357-359 (2000).
Office Action issued in Chinese Application No. 200880014725.9 dated May 29, 2012.
Indian Office Action mailed on Aug. 29, 2013, in corresponding Indian Patent Application 5942/DELNP/2009.

* cited by examiner

*Primary Examiner* — Allison Fox
*Assistant Examiner* — Yvonne Pyla
(74) *Attorney, Agent, or Firm* — Buchanan, Ingersoll & Rooney PC

(57) ABSTRACT

The present invention discloses a powdery lipase preparation which is a granulated material comprising a lipase derived from *Rhizopus oryzae* and/or a lipase derived from *Rhizopus delemar* and a soybean powder having a fat content of 5 mass % or more. A lipase activity is improved by using this powdery lipase preparation.

9 Claims, 1 Drawing Sheet

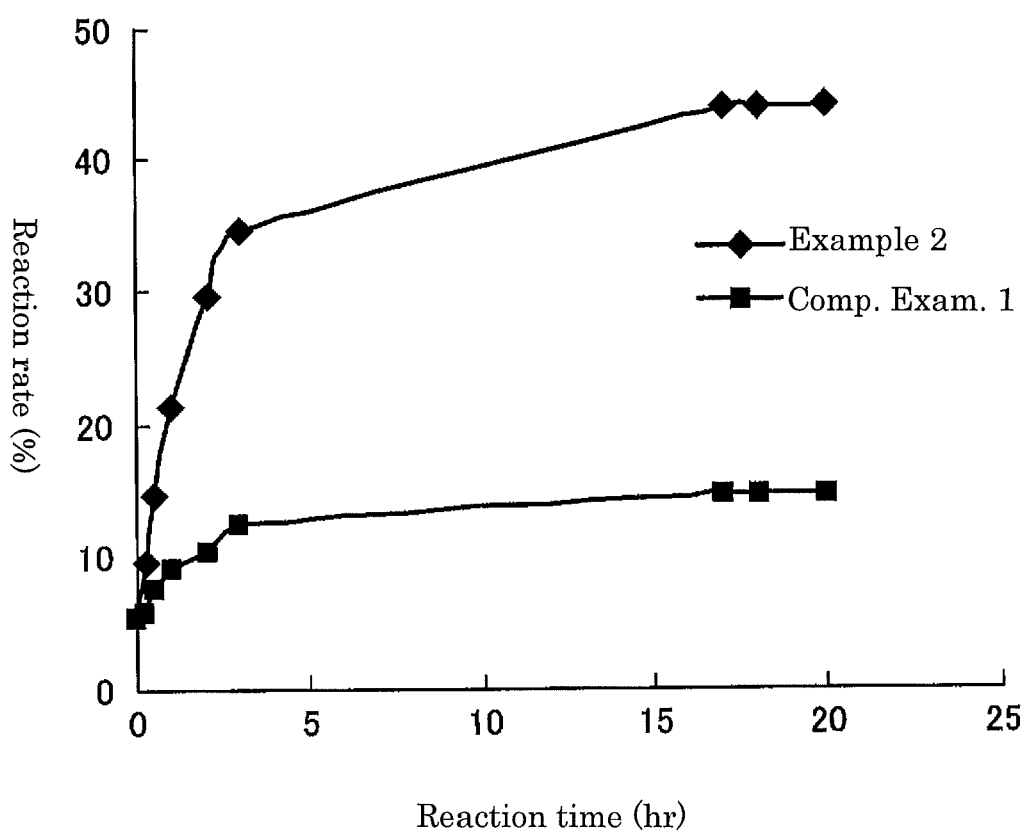

POWDERY LIPASE PREPARATION, METHOD FOR PRODUCING THE SAME AND USE THEREOF

TECHNICAL FILED OF THE INVENTION

The present invention relates to a powdery lipase preparation which can be preferably used in various esterification reactions or transesterification reactions, and a powdery lipase preparation which comprises esters of fatty acids and/or fatty acids; method for producing the same; and method of transesterification using said powdery lipase preparations.

BACKGROUND OF THE INVENTION

Lipases are widely used in esterification of various carboxylic acids such as fatty acids with alcohols such as monoalcohols and polyalcohols, transesterification between esters of several carboxylic acids, and the like. Among them, the transesterification reaction is an important technology not only as method for modifying animal and vegetable fats and oils but also as method for producing esters of various fatty acids such as sugar esters and sterol esters. When a lipase, which is an enzyme hydrolyzing fats and oils, is used as a catalyst in the above reactions, the transesterification reaction can be conducted under the mild condition, i.e. at room temperature to about 70° C. Therefore, the reactions using a lipase can better inhibit side reactions and reduce energy costs as compared with the conventional chemical reactions. In addition to it, since a lipase as a catalyst is a natural product, it is highly safe. Further, intended compounds can be effectively produced by using a lipase due to the substrate specificity and positional specificity thereof. However, even if a powdery lipase is used in the transesterification reaction without change, activity thereof does not fully express. Besides, it is difficult to uniformly disperse a basically water-soluble lipase into oil raw materials and to collect such a lipase.

Therefore, generally, it is common to immobilize a lipase to some carriers, such as an anion-exchange resin (Patent Literature 1), a phenol adsorption resin (Patent Literature 2), a hydrophobic carrier (Patent Literature 3), a cation-exchange resin (Patent Literature 4) and a chelate resin (Patent Literature 5) and to use it in the reactions such as esterification and transesterification. Further, the method for producing immobilized lipase particles is proposed which comprises the steps of producing an emulsion wherein a water phase dissolving a lipase and a substance which acts as a carrier of a lipase is dispersing into a hydrophobic phase; and removing water from the emulsion to convert the water phase into solid particles thereof covered with the lipase (Patent Literature 6).

As mentioned above, a lipase has been conventionally immobilized and used in the transesterification reaction. However, the immobilized lipase loses an original lipase activity through the immobilization. In addition to it, when a porous carrier is used, a raw material or a product gets stuck in fine pores and, as a result, the transesterification rate decreases. Further, in the transesterification reaction wherein the conventional immobilized lipase is used, water which a carrier retains is brought into the reaction system, and therefore, it has been difficult to prevent side reactions such as production of diglycerides and monoglycerides in the transesterification reaction of fats and oils.

In light of the above situations, various technologies using a powdery lipase have been developed. For example, the method of the transesterification reaction is proposed which comprises the steps of dispersing a powdery lipase, in the presence or absence of an inactive organic solvent(s), into a raw material comprising an ester(s) so that 90% or more of the dispersed powdery lipase particles maintains a particle diameter of 1-100 μm during the reaction; and transesterifying said mixture (Patent Literature 7). Further, use of an enzymatic powder is also proposed, said enzymatic powder which is obtained by drying an enzyme solution comprising phospholipids and lipid-soluble vitamins (Patent Literature 8).

However, a powdery lipase of which lipase activity is further improved has been desired.

On the other hand, the method for producing an enzyme-immobilized preparation is proposed which comprises the steps of adding a grain powder or a grain powder and sugars to a solution comprising an enzyme(s), and drying the solution comprising an enzyme(s) (Patent Literature 9). The literature discloses that examples of usable enzymes include a lipase, a cellulase, a protease, an amylase and a pectinase, and that the enzyme-immobilized preparation obtained by the above production method can inhibit enzyme deactivation in the presence of a substance reducing an enzymatic activity. However, there is no description on the improvement of an enzymatic activity therein. Further, actually produced examples in the literature are only those in which a defatted soybean powder having less fat content is applied as a cellulase or a protease, and there is no specific description on an example wherein a lipase is used.

Patent Literature 1: JP-A 60-98984
Patent Literature 2: JP-A 61-202688
Patent Literature 3: JP-A 2-138986
Patent Literature 4: JP-A 3-61485
Patent Literature 5: JP-A 1-262795
Patent Literature 6: JP-B 3403202
Patent Literature 7: JP-B 2668187
Patent Literature 8: JP-A 2000-106873
Patent Literature 9: JP-A 11-246893

DISCLOSURE OF THE INVENTION

The object of the present invention is to provide a powdery lipase preparation of which lipase activity is improved.

The additional object of the present invention is to provide a method for producing the powdery lipase preparation.

The further additional object of the present invention is to provide a method of transesterification or a method of esterification in which the powdery lipase preparation is used.

The present invention has been completed based on the finding that, when granulating a lipase of specific origin into a powder with a soybean powder having a high fat content and using the obtained powdery lipase preparation in the esterification reaction and/or the transesterification reaction, the lipase activity thereof is drastically improved.

Namely, the present invention provides a powdery lipase preparation which is a granulated material comprising a lipase derived from *Rhizopus oryzae* and/or a lipase derived from *Rhizopus delemar* and a soybean powder having a fat content of 5 mass % or more.

The present invention also provides a method for producing a powdery lipase preparation which comprises the step of drying an aqueous solution wherein a lipase derived from *Rhizopus oryzae* and/or a lipase derived from *Rhizopus delemar* and a soybean powder having a fat content of 5 mass % or more are dissolved or dispersed.

The present invention further provides a method for producing a transesterified product or an esterified product which comprises the step of transesterifying or esterifying one or more kinds selected from esters of fatty acids, fatty acids and alcohols using the above powdery lipase preparation.

According to the present invention, it is possible to provide a powdery lipase preparation having a drastically improved enzymatic activity by which the transesterification or esterification reaction can be effectively conducted, and said powdery lipase preparation which can be reused by being collected after the reaction.

Further, according to the present invention, it is also possible to obtain a powdery lipase preparation which can be safely and inexpensively used in producing foods or food additives for those who cannot take proteins or fats and oils derived from animals because of religious or health reasons.

BRIEF DESCRIPTION OF THE DRAWINGS

FIG. 1 shows changes over time of the transesterification reaction rate when using a powdery lipase preparation obtained by Example 2 (invention 1) and when using a conventional powdery lipase preparation.

BEST MODE FOR CARRYING OUT THE INVENTION

*Rhizopus delemar* and *Rhizopus oryzae* of *Rhizopus* sp. can be used as a lipase used in the present invention. A lipase of the present invention is preferably a 1,3-specific lipase.

Examples of a lipase include Picantase R8000 (a product of Robin) and Lipase F-AP15 (a product of Amano Enzyme Inc.). The most preferable lipase is Lipase DF "Amano" 15-K (also referred to as Lipase D) derived from *Rhizopus oryzae*, a product of Amano Enzyme Inc. This product is a powdery lipase. Meanwhile, Lipase DF "Amano" 15-K was originally referred to as a lipase derived from *Rhizopus delemar*.

A lipase used in the present invention can be those obtained by drying an aqueous solution containing a lipase, such as an aqueous solution containing a medium component of a lipase.

A soybean powder having a fat content of 5 mass % or more which is used in the present invention preferably has a fat content of 10 mass % or more and more preferably has a fat content of 15 mass % or more, and on the other hand, preferably has a fat content of 25 mass % or less. It is particularly preferably a soybean powder having a fat content of 18-23 mass %. Examples of fats include fatty acid triglycerides and analogs thereof. The fat content of soybeans can be easily measured by the method such as Soxhlet extraction and the like.

In the present invention, a whole fat soybean powder can be used as such a soybean powder. It is also possible to use soymilk as a raw material of a soybean powder. A soybean powder can be produced by crushing soybeans in accordance with the ordinary method, and the particle diameter thereof is preferably around 0.1-600 μm.

The usage of a soybean powder per a lipase is preferably 0.1-200 times by mass standard, more preferably 0.1-20 times, and most preferably 0.1-10 times.

A powdery lipase preparation of the present invention preferably has a water content of 10 mass % or less, and particularly preferably 1-8 mass %.

A particle diameter of a powdery lipase preparation of the present invention can be arbitrarily selected, and 90 mass % or more of the powdery lipase preparation preferably has a particle diameter of 1-100 μm. The average particle diameter thereof is preferably 10-80 μm. Further, a form of the powdery lipase preparation is preferably spherical.

The particle diameter of a powdery lipase preparation can be measured by using a particle size distribution analyzer (LA-500) of HORIBA, Ltd, for example.

A powdery lipase preparation of the present invention can be produced by the method comprising the step of drying an aqueous solution wherein a lipase and a soybean powder are dissolved or dispersed, and said drying is one kind of the methods selected from spray drying, freeze drying, and solvent precipitation/drying.

An aqueous solution wherein a lipase and a soybean powder are dissolved or dispersed can be obtained by dissolving and dispersing a powdery lipase and a soybean powder in water; by mixing a powdery lipase in an aqueous solution wherein a soybean powder is dissolved or dispersed; or, as mentioned below, by mixing a soybean powder in an aqueous solution containing a lipase.

In the process of drying an aqueous solution wherein a lipase and a soybean powder are dissolved or dispersed, particles of a lipase and/or those of a soybean powder agglutinate to form a granulated material comprising a lipase and a soybean powder. This granulated material can comprise the medium component of a lipase.

Thus prepared powdery lipase preparation can be used in transesterification or esterification without change.

The mass of water in an aqueous solution wherein a lipase and a soybean powder are dissolved or dispersed is adjusted corresponding to a total mass of a lipase and a soybean powder. More specifically, the mass of water per a total mass of a lipase and a soybean powder is preferably 0.5-1,000 times, more preferably 1.0-500 times and most preferably 3.0-100 times.

Particularly, when producing a powdery lipase preparation by spray drying, the mass of water per a total mass of a lipase and a soybean powder is preferably 2.0-1,000 times, more preferably 2.0-500 times and most preferably 3.0-100 times because of the characteristic of the spray dryer. Meanwhile, when an aqueous solution containing a lipase is used as a raw material and a lipase content in said aqueous solution is unclear, the lipase content is obtained by powderizing the aqueous solution containing a lipase by freeze drying or other drying method under reduced pressure, and the mass of a lipase can be calculated based on the obtained lipase content.

Examples of an aqueous solution containing a lipase include a lipase culture from which fungus body is removed, a purified culture, an aqueous solution wherein a lipase obtained from said culture(s) is dissolved or dispersed again, an aqueous solution wherein a marketed powdery lipase is dissolved or dispersed again, and a marketed liquid lipase. Further, the aqueous solutions from which a low-molecular-weight component such as salts is removed are more preferable in order to further improve a lipase activity. In addition, the aqueous solutions from which a low-molecular-weight component such as sugars is removed are more preferable in order to further improve powder properties.

Examples of a lipase culture include aqueous solutions containing soybean flour, peptone, corn steep liquor, $K_2HPO_4$, $(NH_4)_2SO_4$, $MgSO_4 \cdot 7H_2O$ or the like. The concentrations thereof are as follows: soybean flour is 0.1-20 mass % and preferably 1.0-10 mass %; peptone is 0.1-30 mass % and preferably 0.5-10 mass %; corn steep liquor is 0.1-30 mass % and preferably 0.5-10 mass %; $K_2HPO_4$ is 0.01-20 mass % and preferably 0.1-5 mass %; $(NH_4)_2SO_4$ is 0.01-20 mass % and preferably 0.05-5 mass % and $MgSO_4 \cdot 7H_2O$ is 0.01-20 mass % and preferably 0.05-5 mass %. The cultural conditions thereof can be controlled as follows: the cultural temperature is 10-40° C. and preferably 20-35° C.; the quantity of airflow is 0.1-2.0VVM and preferably 0.1-1.5VVM; the rotation speed for stirring is 100-800 rpm and preferably 200-400 rpm; pH is 3.0-10.0 and preferably 4.0-9.5.

The separation of a fungus body is preferably conducted by centrifugation, membrane filtration, or the like. The removal of low-molecular-weight components such as salts and sugars can be treated with ultrafiltration membranes. More specifically, after the treatment with ultrafiltration membranes, an aqueous solution containing a lipase is concentrated so as to become ½ volume thereof; and then, the same amount of a phosphate buffer as that of the concentrated solution is added thereto. By repeating these procedures 1-5 times, it is possible to obtain an aqueous solution containing a lipase from which a low-molecular-weight component is removed.

The centrifugal force of the centrifugation is preferably controlled to 200-20,000×g. Similarly, the pressure of the membrane filtration is preferably controlled to 3.0 kg/m² or less in microfiltration membranes, the filter press and the like. In the case of enzymes in the fungus body, it is preferable to crush cells thereof by a homogenizer, Waring blender, ultrasonic disruption, French press, ball mill or the like, and then to remove cell residues by centrifugation, membrane filtration, or the like. The rotation speed for stirring of the homogenizer is 500-30,000 rpm and preferably 1,000-15,000 rpm. The rotation speed of Waring blender is 500-10,000 rpm and preferably 1,000-5,000 rpm. The time for stirring is 0.5-10 minutes and preferably 1-5 minutes. The ultrasonic disruption is conducted in the condition of 1-50 KHz and preferably 10-20 KHz. It is preferable that the ball mill has glass pellets having the diameter of 0.1-0.5 mm.

In some stage before the drying process, it is possible to concentrate an aqueous solution containing a lipase. The concentration method is not particularly limited, and examples thereof include an evaporator, a flash evaporator, the concentration by ultrafiltration, the concentration by microfiltration, salting out by inorganic salts, precipitation with solvents, absorption with ion-exchange celluloses and the like, and water absorption with water-absorbing gels. The concentration by ultrafiltration and an evaporator are preferable among them. The module of the concentration by ultrafiltration is as follows: a flat membrane or a hollow fiber membrane each having a fractionated molecular weight of 3,000-100,000 and more preferably 6,000-50,000; and the material thereof is preferably polyacrylonitrile, polysulphone, or the like.

Next, spray drying, freeze drying and solvent precipitation/drying are described herein, each of which is the method for drying an aqueous solution wherein a lipase and a soybean powder are dissolved or dispersed.

Spray drying is preferably conducted by using spray dryers such as a countercurrent flow dryer with a nozzle(s), a countercurrent flow dryer with a disk, a concurrent flow dryer with a nozzle(s) and a concurrent flow dryer with a disk. The concurrent flow dryer with a disk is more preferable, and it is preferable to control the conditions as follows in spray drying: the rotation speed of the atomizer is 4,000-20,000 rpm; and heating is 100-200° C. for inlet temperature and 40-100° C. for outlet temperature. Particularly, it is preferable to adjust the temperature of an aqueous solution containing a lipase and a soybean powder to 20-40° C., and then to spray dry the solution in dry atmosphere of 70-130° C. It is also preferable to adjust pH of the aqueous solution to 7.5-8.5 before drying.

Freeze drying is preferably conducted by using a bench-top freeze dryer for a small quantity of sample, a plate type freeze dryer, or the like. Further, it is also possible to dry the solution under reduced pressure.

Solvent precipitation/drying is conducted by the method comprising the steps of gradually adding an aqueous solution wherein a lipase and a soybean powder are dissolved or dispersed to a solvent to generate a precipitate, centrifuging the obtained precipitate with a centrifuge to collect it, and then drying the collected precipitate under reduced pressure. A sequence of operations is preferably conducted under the low-temperature condition of room temperature or lower, in order to prevent denaturalization and/or deterioration of a powdery lipase preparation.

Examples of a solvent used in the solvent precipitation include water-soluble or hydrophilic solvents such as ethanol, acetone, methanol, isopropyl alcohol and hexane, and mixed solvents thereof are also usable. Among them, ethanol or acetone is preferably used in order to further enhance the activity of a powdery lipase preparation.

Though the amount of the used solvent is not particularly limited, it is preferable to use 1-100 times by volume of the solvent per a volume of an aqueous solution wherein a lipase and a soybean powder are dissolved or dispersed, and it is more preferable to use 2-10 times by volume of the solvent.

After the solvent precipitation, a precipitate can be obtained by filtration after standing, and it can also be obtained by moderate centrifuging of around 1,000-3,000×g. The drying of the obtained precipitate can be conducted, for example, by drying under reduced pressure.

In the present invention, esters of fatty acids and/or fatty acids can be further added in the process of producing a powdery lipase preparation. More specifically, a powdery lipase preparation can be obtained by the method comprising the steps of contacting esters of fatty acids and/or fatty acids to an aqueous solution wherein a lipase and a soybean powder are dissolved or dispersed, and drying the mixture. The lipase activity and the stability of a powdery lipase preparation can be further improved by contacting esters of fatty acids and/or fatty acids as mentioned above.

Examples of esters of fatty acids include esters of fatty acids between monoalcohols or polyalcohols and fatty acids. The esters of fatty acids of polyalcohols may be partial esters or full esters.

Examples of monoalcohols include alkyl monoalcohols and sterols such as phytosterols. An alkyl part constituting alkyl monoalcohols is preferably a medium-chain alkyl having 6-12 carbon atoms or a long-chain alkyl having 13-22 carbon atoms, each of which is saturated or unsaturated, and linear or branched. Phytosterols are preferably sitosterol, stigmasterol, campesterol, fucosterol, spinasterol, brassicasterol, and the like. Examples of polyalcohols include glycerin condensates such as glycerin, diglycerin, and decaglycerin, glycols such as propylene glycol, and sorbitol.

Though the constituent fatty acids of the used esters of fatty acids and the used fatty acids are not particularly limited, fatty acids derived from fats and oils are preferable. Examples thereof include medium-chain fatty acids having 6-12 carbon atoms, e.g. a hexanoic acid, an octane acid, a decane acid, and an undecanoic acid; and long-chain unsaturated fatty acids having 13-22 carbon atoms, e.g. an oleic acid, a linoleic acid, a linolenic acid, a ricinoleic acid, and an erucic acid. The examples also include long-chain saturated fatty acids, e.g. a tetradecanoic acid, a hexadecanoic acid, an octadecanoic acid, an eicosanoic acid and a docosanoic acid.

The used esters of fatty acids are preferably one or more kind(s) selected from the group consisting of diglycerides and monoglycerides each of which comprises fats and oils or fatty acids derived from fats and oils as constituents. Further, it is also possible to use a mixture of fatty acids and partial esters obtained by hydrolyzing a part of esters of fatty acids.

Meanwhile, it is preferable to select the same esters of fatty acids and fatty acids used in a powdery lipase preparation as raw materials used in transesterification or esterification using a powdery lipase preparation.

The fats and oils used as esters of fatty acids are not particularly limited, and when producing a powdery lipase preparation by conducting hydrolysis and esterification, it is preferable to use liquid fats and oils at reaction temperature.

Examples of fats and oils include one or mixtures of two or more kinds selected from the groups consisting of; vegetable fats and oils such as canola oil, sunflower oil, olive oil, corn oil, palm oil, sesame-seed oil, safflower oil, soybean oil, and higholeic fats and oils, cotton seed oil, rice oil, linseed oil, palm oil, fractionated oil of palm oil, palm kernel oil, camellia oil, cacao butter, shea butter, sal butter and illipe butter; triglycerides (synthetic fats and oils) such as triolein (glycerol trioleate), tricaprylin (glycerol trioctanoate), triacetin (glycerol triacetate) and tributyrin (glycerol tributanoate); and animal fats and oils such as fish oil, beef tallow and lard. Vegetable fats and oils are preferable among them.

When using esters of fatty acids, or esters of fatty acids and fatty acids as raw materials, a powdery lipase preparation can be produced by the method comprising the steps of adding and contacting esters of fatty acids, or esters of fatty acids and fatty acids to an aqueous solution wherein a lipase and a soybean powder are dissolved or dispersed, uniformly stirring the mixture with a stirrer, a three-one motor, or the like to hydrolyze and/or emulsify or disperse it, and then drying the mixture by one kind of the methods selected from spray drying, freeze drying, and solvent precipitation/drying.

It is also possible to dry the mixture by dehydration accompanying the esterification reaction. Namely, a powdery lipase preparation can be produced by the method comprising the steps of hydrolyzing and/or emulsifying and dispersing the mixture, then conducting the esterification reaction to the mixture with dehydrating it, and, if necessary, filtering an oil part thereof such as unreacted substances.

The additive amount of esters of fatty acids and/or fatty acids used in the production of a powdery lipase preparation is preferably 0.1-500 times by mass per a total mass of a lipase and a soybean powder, more preferably 0.2-100 times by mass, and most preferably 0.3-50 times by mass.

Meanwhile, when producing a powdery lipase preparation by spray drying, the additive amount of the used esters of fatty acids and/or fatty acids per a total mass of a lipase and a soybean powder is preferably 0.1-10 times by mass, more preferably 2.0-10 times by mass and most preferably 3.0-10 times by mass. This is because, in the case of using a spray dryer, when the additive amount of esters of fatty acids and/or fatty acids becomes larger, there are problems that water insufficiently evaporates or that it becomes difficult to collect the obtained powdery lipase preparation due to excess esters of fatty acids and/or fatty acids.

Though the upper limit of the additive amount of the used esters of fatty acids and/or fatty acids can be set higher corresponding to modification of devices for spray drying or changes of collection forms, in case of comprising esters of fatty acids and/or fatty acids beyond necessity, filtration process is required.

When producing a powdery lipase preparation comprising esters of fatty acids and/or fatty acids by solvent precipitation, it is preferable, as an amount of the used solvent, to use 1-100 times by volume of the solvent per a total mass of esters of fatty acids and/or fatty acids and an aqueous solution wherein a lipase and a soybean powder are dissolved or dispersed, and more preferable to use 2-10 times by volume of the solvent.

When adding a following filter aid before conducting the solvent precipitation, a mass of the filter aid is further included in the above total mass, and the solvent is used based on said total mass.

In the present invention, a process of adding a filter aid can be further included therein.

When drying is conducted by dehydration accompanying the esterification reaction, it is possible to add a filter aid before, during or after the esterification reaction. It is preferable to add a filter aid since filtration can be smoothly conducted after the esterification reaction.

When adding a filter aid before or during the esterification reaction, it is possible to further add fats and oils at that time. Since the viscosity of a solution increases by the addition thereof, in case stirring does not proceed smoothly, the flowability of a reaction solution is improved by adding fats and oils as mentioned above.

Examples of usable filter aids include silica gel, sellite, cellulose, starch, dextrin, activated carbon, activated earth, kaolin, bentonite, talc and sand. Silica gel, sellite and cellulose are preferable among them. The particle diameter of a filter aid can be arbitrarily selected, and 1-100 µm is preferable and 5-50 µm is particularly preferable.

The filter aid usable before, during or after the esterification reaction is preferably added in an amount of 1-500 mass % per a total mass of a lipase and a soybean powder, and more preferably in an amount of 10-200 mass %. When using the filter aid in the amount within the above range, the load in the filtration becomes less, and a large-scale filtration device or pretreatment for filtration such as a high-performance centrifuge is not required.

Further, it is also possible to comprise a filter aid in a powdery lipase preparation of the present invention which is obtained by the drying method other than dehydration accompanying the esterification reaction. When obtaining a powdery lipase preparation by spray drying or freeze drying, a filter aid can be added before or after the drying.

When the drying is conducted after the solvent precipitation, it is preferable to add a filter aid to a powdery lipase preparation obtained by drying.

The amount of a filter aid comprised in the obtained powdery lipase preparation can be 1-500 mass % based on a total mass of a lipase and a soybean powder, and preferably 10-200 mass %.

Next, described herein is the method for producing a transesterified product or an esterified product each of which is obtained by conducting transesterification or esterification using a powdery lipase preparation of the present invention.

The transesterification reaction conducted using a powdery lipase preparation of the present invention is a transesterification reaction of esters of fatty acids with one or more kinds selected from esters of fatty acids, fatty acids and alcohols. Examples thereof include transesterification between fats and oils in accordance with the ordinary method, transesterification of fats and oils with esters of fatty acids, and transesterification of alcoholysis or acidolysis.

Further, the esterification reaction conducted by using a powdery lipase preparation of the present invention is an esterification reaction of partial esters of fatty acids with fatty acids, or an esterification reaction of mono- or poly-alcohols with fatty acids. Examples thereof include an esterification reaction of glycerin with fatty acids.

More specifically, as the transesterification reaction between fats and oils, it is possible to transesterify canola oil which is a triglyceride of a long-chain fatty acid and a glycerol trioctanoate which is a triglyceride of a medium-chain fatty acid derived from vegetables, and to produce a triglyceride which comprises long-chain and medium-chain fatty acids.

Further, as the transesterification reaction of fats and oils and fatty acids using acidolysis, it is possible to produce structured fats and oils wherein a 1,3-specific lipase that a lipase has is significantly used. This is the method that a specific fatty acid is left on the second position of glycerin skeleton and fatty acids on the first and third positions are replaced by intended fatty acids. The obtained fats and oils can be used as those for chocolates and those having specific nutritional effects.

The condition of the transesterification reaction or the esterification reaction using a powdery lipase preparation is not particularly limited, and each reaction can be conducted by the ordinary method.

Generally, the reaction is conducted under ordinary or reduced pressure with preventing contamination of water that causes hydrolysis. Though the reaction temperature depends on a used raw material and the freezing point of a mixture in which a raw material is combined, it is preferably 20-80° C., and if not limited by the freezing point, it is preferably 40-60° C.

The additive amount of a powdery lipase preparation in a reaction raw material is preferably 0.05-10 mass %, and more preferably 0.05-5 mass %. The most suitable amount is determined in accordance with the reaction temperature, set reaction time, activity of the obtained powdery lipase preparation, and the like. After the reaction completed, a powdery lipase preparation is removed by filtration and centrifugation, and it can be repeatedly used (evaluation of stability) until the activity thereof decreases to the extent that the production of a powdery lipase preparation is impossible.

Accordingly, it is preferable that a lipase, which is usually expensive, can give both high activity and high stability in the smallest possible amount thereof to a powdery lipase preparation.

Though thus obtained transesterified or esterified material is not particularly limited, it is preferably transesterified or esterified fats and oils used in the food field, and more preferably transesterified or esterified fats and oils derived from vegetable oils which can be used in producing foods or food additives for those who cannot take proteins or fats and oils derived from animals because of religious or health reasons.

Next, Production examples and Examples will further illustrate the present invention.

Example 1

Three times amount of soymilk (a dispersion of soybean powder having 20 mass % fat content: Meiraku Co., Ltd.) was added with stirring to an enzyme solution (150000 U/mL) of Lipase DF "Amano" 15-K (also referred to as Lipase D), a product of Amano Enzyme Inc. Then, pH thereof was adjusted to 7.8 with a 0.5N NaOH solution (solution temperature: room temperature), and the mixture was sprayed at inlet temperature of 130° C. to conduct spray drying (with SD-1000, Tokyo Rikakikai Co., Ltd). 95 mass % of the obtained powdery lipase preparation had a particle diameter of 1-100 μm.

Comparative Example 1

A powdery lipase preparation was obtained by the same method as that of Example 1 except that soymilk was not added.

The activity of each powdery lipase preparation obtained in Example 1 and Comparative Example 1 was measured in accordance with the following method.

Measurement Method of Lipase Activity

Each powdery lipase preparation was added to oil in which 1,2,3-trioleoyl glycerol and 1,2,3-trioctanoyl glycerol were mixed in 1:1(w), and reacted at 60° C. 10 μL thereof was taken as a sample over time, diluted with 1.5 mL of hexane, and a solution wherein the powdery lipase preparation was filtered was taken as a sample for gas chromatography (GC). The solution was analyzed by GC (column: DB-1ht) and the reaction rate was calculated from the following formula. The GC conditions are: column temperature: 150° C., temperature rising: 15° C./min., and final temperature 370° C.

Reaction rate (%)={$C34$area/($C24$area+$C34$area)}×100 wherein, C24 is 1,2,3-trioctanoyl glycerol; C34 is 1,2,3-trioctanoyl glycerol wherein one fatty acid is replaced by an oleic acid; and area is each area thereof. Based on the reaction rate of each time, the reaction rate constant k was calculated by an analysis software (origin ver. 6.1).

The activity of the powdery lipase preparation was represented by the relative activity when defining value k of a spray-dried enzyme solution without change as 100.

Table 1 shows results thereof.

TABLE 1

|  | Condition (volume ratio) | Relative activity (%) |
| --- | --- | --- |
| Comp. Exam. 1 | lipase solution | 100 |
| Example 1 | lipase solution:soymilk = 1:3 (pH 7.8) | 504 |

From the results of Table 1, it is clarified that a lipase activity is drastically improved according to the present invention.

Example 2

Three times amount of 10% aqueous solution of a deodorized whole fat soybean powder (fat content: 23 mass %; trade name: Alphaplus HS-600, produced by Nisshin Cosmo Foods, Ltd.) was added with stirring to the same enzyme solution (150000 U/mL) of Lipase DF "Amano" 15-K as that of Example 1. Then, pH thereof was adjusted to 7.8 with a 0.5N NaOH solution, and the mixture was spray dried (with SD-1000, Tokyo Rikakikai Co., Ltd) (invention 1).

When comparing each aqueous solution of a deodorized whole fat soybean powder having the concentration of 10 mass % (hereinafter referred to as %), 15% (invention 2) and 20% (invention 3), a powder of which transesterifying activity is highest was able to be obtained by adding 10% aqueous solution thereof.

Further, when autoclave sterilization (121° C., 15 mins.) was previously conducted to 10% solution of a deodorized whole fat soybean powder and the solution was cooled down to room temperature and powderized in accordance with the above process (invention 4), an enzymatic powder having the further higher activity was able to be obtained.

Table 2 shows results thereof.

TABLE 2

|  | Condition (volume ratio) | Relative activity (%) |
| --- | --- | --- |
| Invention 1 | lipase solution:10% HS-600 = 1:3(pH 7.8) | 409 |
| Invention 2 | lipase solution:15% HS-600 = 1:3(pH 7.8) | 209 |
| Invention 3 | lipase solution:20% HS-600 = 1:3(pH 7.8) | 227 |
| Invention 4 | lipase solution:10% HS-600 = 1:3(pH 7.8) | 440 |

Example 3

The kind of a soybean flour added to the same enzyme solution (150000 U/mL) of Lipase DF "Amano" 15-K as that of Example 1 was examined. The concentration of an aqueous solution of a soybean flour was set to 10%.

A powdery lipase preparation was prepared by the same method as that of Example 1 except that a U.S. soybean flour (trade name: Organic Soy Flour produced by Arrowhead Mills; after preparing slurry thereof with a mixer, straining it with gauze or the like, and the obtained solution is used; fat content: 7 mass %) or a defatted soybean powder (trade name: Soya Flour FT-N produced by Nisshin Cosmo Foods, Ltd.; fat content: 0.2 mass %, comparative example 2) was used.

Table 3 shows a lipase activity of each obtained powdery lipase preparation.

TABLE 3

|  | Condition (volume ratio) Relative | Relative activity (%) |
|---|---|---|
| Example 3 | lipase solution:10% US soy flour (pH 7.8) | 465 |
| Comp. Exam. 2 | lipase solution:10% defatted soy powder (pH 7.8) | 22 |

From the results of Table 3, it is clarified that a lipase activity cannot be improved when using a defatted soybean powder having less fat content.

Example 4

2 g of the powdery lipase preparation obtained in Example 2 (invention 1) was added to 200 g of shea olein (trade name: Lipex205 produced by Aarhuskarlshamn), and stirred at 60° C. for 20 hours to conduct the transesterification reaction. 10 μL thereof was taken as a sample over time, diluted with 1.5 mL of hexane, and a solution wherein the powdery enzyme was filtered was taken as a sample for gas chromatography (GC). The ratio of distearoyl monooleoyl glycerol (a mixture of SSO and SOS) in the triacylglyceride composition was defined as the reaction rate. Similarly, the transesterification reaction was conducted to the powdery lipase preparation obtained in Comparative Example 1. As a result, as shown in FIG. 1, it was clarified that the activity of the enzyme obtained in Example 2 was obviously high.

What is claimed is:

1. A powdery lipase preparation which is a granulated material comprising a lipase derived from *Rhizopus delemar* and a soybean powder having a fat content of 5 mass % or more, wherein the soybean powder is a whole fat soybean powder and wherein the soybean powder per a lipase is 0.1 to 20 times by mass.

2. The powdery lipase preparation according to claim 1, wherein the fat content of the soybean powder is 10-25 mass %.

3. The powdery lipase preparation according to claim 1, wherein 90 mass % or more of the powdery lipase preparation has a particle diameter of 1-100 μm.

4. The powdery lipase preparation according to claim 1 for transesterification or esterification.

5. A method for producing a powdery lipase preparation which comprises the step of drying an aqueous solution wherein a lipase derived from *Rhizopus delemar* and a soybean powder having a fat content of 5 mass % or more are dissolved or dispersed.

6. The method according to claim 4, which comprises the step of adjusting pH of the aqueous solution to 7.5-8.5 before drying.

7. The method according to claim 5, wherein the drying is conducted by spray drying.

8. The method according to claim 5, which comprises adjusting the temperature of the aqueous solution comprising the lipase and the soybean power to 20-40° C. just before spray drying; and spraying the solution in dry atmosphere of 70-130° C.

9. A method for producing a transesterified product or an esterified product which comprises the step of transesterifying one or more kinds of esters of fatty acids, or esterifying fatty acids and alcohols using the powdery lipase preparation according to claim 1.

* * * * *